United States Patent [19]

Boehm et al.

[11] Patent Number: 5,734,107

[45] Date of Patent: Mar. 31, 1998

[54] ACCELERATION SENSOR

[75] Inventors: Herbert Boehm, Wannweil; Ulrich Goebel, Reutlingen; Franz Schmich, Pfullingen; Gerald Hopf, Reutlingen; Roland Feucht, St. Johann; Albert-Andreas Hoebel, Reutlingen; Botho Ziegenbein, Reutlingen; Bernd Maihoefer, Reutlingen, all of Germany

[73] Assignee: Robert Bosch GmbH, Stuttgart, Germany

[21] Appl. No.: 624,563

[22] PCT Filed: Jul. 20, 1995

[86] PCT No.: PCT/DE95/00953

§ 371 Date: Jun. 28, 1996

§ 102(e) Date: Jun. 28, 1996

[87] PCT Pub. No.: WO96/05515

PCT Pub. Date: Feb. 22, 1996

[30] Foreign Application Priority Data

Aug. 9, 1994 [DE] Germany .................. 44 28 124.2

[51] Int. Cl.$^6$ .................. G01P 15/09; H01L 41/08; H04R 17/00

[52] U.S. Cl. .................. 73/514.34; 73/493; 73/654; 310/329; 29/25.35; 29/621.1

[58] Field of Search .................. 73/514.34, 1 D, 73/763, 781, 855, 856, 774, 775, 777, 493, 654; 29/25.35, 621.1; 310/329, 332, 338

[56] References Cited

U.S. PATENT DOCUMENTS

| | | | |
|---|---|---|---|
| 5,226,325 | 7/1993 | Komurasaki et al. | 73/514.34 |
| 5,239,869 | 8/1993 | Uemura et al. | 73/514.34 |
| 5,452,612 | 9/1995 | Smith et al. | 73/514.34 |

Primary Examiner—Hezron E. Williams
Assistant Examiner—Richard A. Moller
Attorney, Agent, or Firm—Kenyon & Kenyon

[57] ABSTRACT

An acceleration sensor having a piezoelectric sensor element, which is supported as a flexural resonator in a holding module and whose electrodes are connected to an evaluation circuit. The holding module mechanically fixes the sensor element in position and provides, at the same time, for its electrical contacting.

16 Claims, 6 Drawing Sheets

FIG. 7

ACCELERATION SENSOR

FIELD OF THE INVENTION

The present invention relates to an acceleration sensor and more specifically an acceleration sensor having a piezoelectric sensor element which is supported as a flexural resonator in a holding module.

BACKGROUND INFORMATION

Acceleration sensors are generally known. They are employed in motor vehicles, for example, to detect specific accelerative forces acting on the motor vehicle and to provide a control signal as a function of these forces. The control signals are used, e.g., to quickly trigger safety devices, such as airbags, seatbelt tighteners or the like. To this end, the acceleration sensors are equipped with a sensor element, which responds very sensitively to an acceleration occurring in a specific direction. Piezoelectric sensor elements designed as flexural resonators which deflect in response to an occurring acceleration are known. This deflection produces a polarization in the piezoelectric sensor element because of the piezoelectric effect, i.e., a displacement of positive and negative charge carriers leads to the generation of a voltage between two electrodes of the sensor element. These voltage signals can be tapped off and fed to an evaluation circuit. To produce the necessary voltage signals, the piezoelectric sensor elements are comprised of two oppositely poled layers of a piezoceramic material placed in a holding module, which, under the influence of an acceleration, permits a deformation of the sensor element. The disadvantage associated with the known acceleration sensors is that the devices used to accommodate the sensor element and for its electrical contacting are quite complex and, thus, expensive to manufacture. Moreover, it is quite difficult to distinctly specify a sensing direction for the sensor element. This requires auxiliary devices which hold the sensor element in a specific position in relation to a mounting surface.

SUMMARY OF THE INVENTION

In contrast, the acceleration sensor according to the present invention offers the advantage of enabling a precise alignment of the sensor element in a specific sensing direction running, in particular, parallel to a mounting or reference surface and, at the same time, of permitting a mechanical and electrical coupling of the sensor element. Because the module is preferably made of two separate retaining means, which are connected to the evaluation circuit and consist of an electrically conductive material, it is advantageously possible to use these retaining means to mechanically fix the piezoelectric sensor element in position and, at the same time, to electrically contact it. Separate additional measures for stabilizing the position of and for aligning the sensor element, i.e., for tapping off the voltage signals are not needed. Thus, the holding module is able to be produced very simply and cost-effectively.

Additionally, the present invention provides for the holding module to be formed as a blank, which obtains the final shape of the holding module by means of a bending-shaping process, additional mechanical auxiliary stop means, initially joined to the holding module, being available for the assembly operation while the sensor element is introduced into the holding module. The sensor elements are, therefore, able to be introduced quite advantageously in a self-adjusting assembly process into the holding module, it being possible to precisely align the sensor elements in an x-y-z direction and to exactly repeat such alignment during a large-scale production because of the design of the mechanical auxiliary stop means. Thus, acceleration sensors can be produced in a useful, low-cost manufacturing process, so that, under a same acceleration, sensor signals within a narrowly limited scatter range can be expected because of the exact same alignment of the sensor element in each case as a result of the exact same bending bar design. Thus, on the one hand, the interchangeability of the acceleration sensors is facilitated, since they each provide the same signals within narrow tolerance ranges. On the other hand, a tuning of the acceleration sensors to the evaluation circuit is facilitated, as there is no need to individually tune each acceleration sensor, as would be necessary if there was a relatively broad scatter range of sensor signals.

DETAILED DESCRIPTION

Figures 1, 2:
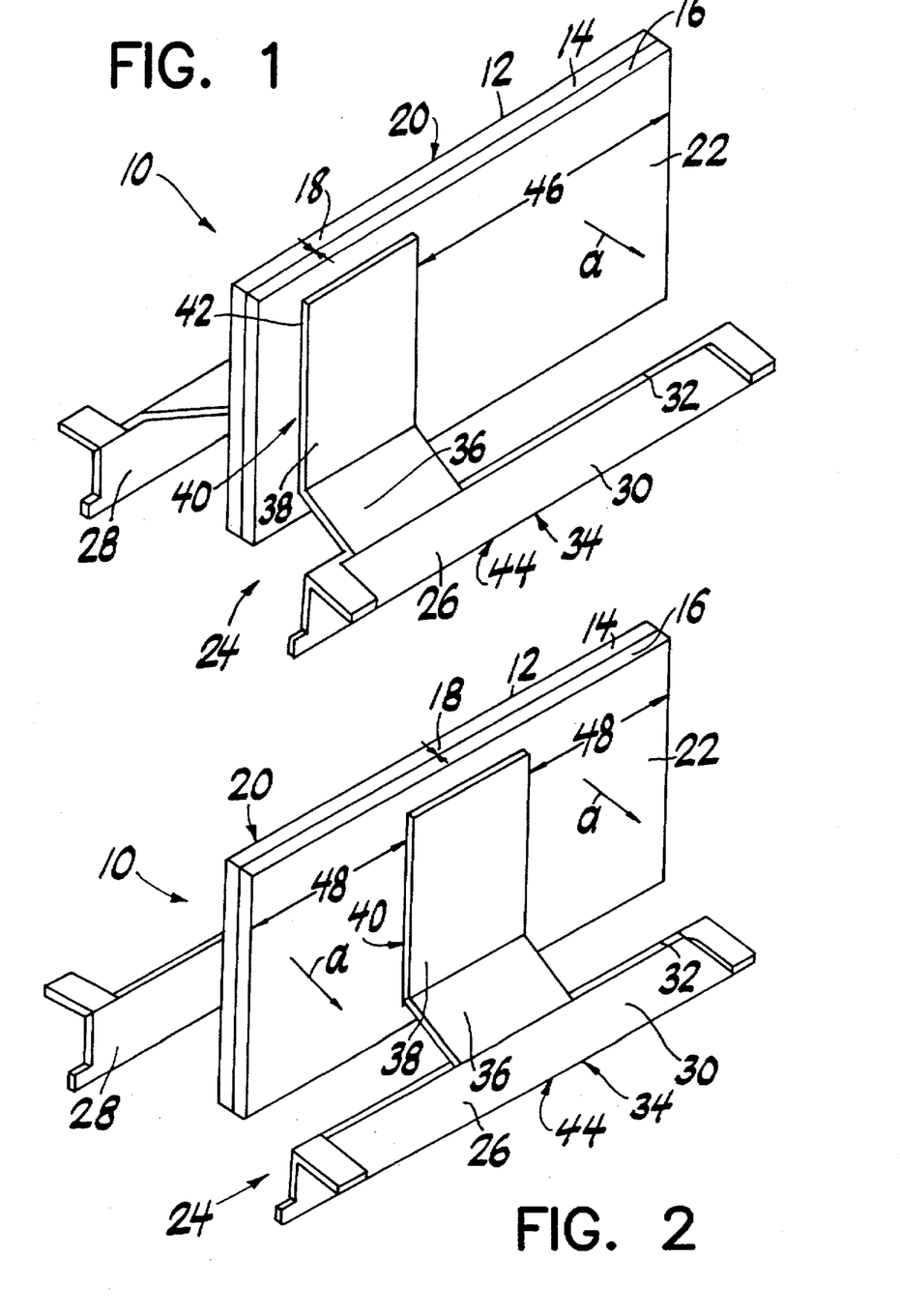
FIG. 1 depicts schematically, a perspective view of an acceleration sensory according to the present invention
FIG. 2 depicts schematically, a perspective view of an acceleration sensor in accordance with a further exemplary embodiment of the present invention

FIG. 1 depicts an acceleration sensor generally denoted by 10. The acceleration sensor 10 has a sensor element 12, which is comprised of a two-layer piezoelectric ceramic. The layers 14 and 16 of the sensor element 12 are thereby so aligned to one another that their polarization directions 18 inside the layers 14 and 16 oppose one another. Overall, therefore, the sensor element 12 is a lamellar-type member. The outer surface of each of the layers 14 and 16 is metallic and forms the electrodes 20 and 22, respectively.

The sensor element 12 is secured in a holding module 24. The holding module 24 is provided for this purpose with two retaining means 26 and 28, which are not mechanically interconnected. The retaining means 26 and 28 can consist, for example, of an electrically conductive strip of material having a corresponding bending contour. The retaining means 26 and 28 have a symmetrical design and are disposed symmetrically to the sensor element 12. The specific design shall now be clarified on the basis of the retaining means 26. Said retaining means 26 has a base member 30 with an essentially lamellar-type construction and an upper end face 32 and a lower end face 34. A retaining web 36 runs at an angle from the upper end face 32 and is integrally formed with an adjustment part 38 running parallel to the sensor element 12. The retaining web 36 and the adjustment part 38 are formed in one piece with the base member 30 and properly shaped in a bending process. The adjustment part 38 essentially has a platelike design and constitutes a first contact region 40 of the retaining means 26. The contact region 40 is mechanically and electroconductively connected to the sensor element 12, in particular to its electrode 22, for example, by applying an adhesive agent 42 therebetween. The lower end face 34 forms a second contact region 44 of the retaining means 26.

The second retaining means 28 has a completely analogous design and, accordingly, likewise has—not shown in FIG. 1—a first contact region 40' formed by an adjustment part 38' and a second contact region 44'. The contact region 40' is likewise mechanically and electroconductively connected by means of for example an adhesive agent 42 to the sensor element 12, and in particular to its electrode 20. Because of the manner in which the sensor element 12 is secured between the adjustment parts 38 and 38' and due to its lamellar-type construction, one obtains a free bending bar denoted here by 46.

The acceleration sensor 10 depicted in FIG. 1 performs the following function:

The acceleration sensor 10 is mounted via its retaining means 26 or 28 on an assembly surface (not shown in FIG. 1), so that the sensor element 12 comes to rest normal to the assembly surface. Under the influence of an acceleration a, indicated here by an arrow, the sensor element 12 experiences a certain deflection of its bending bar 46. How great or small the deflection of the bending bar 46 is dependent on the magnitude of the acceleration a. The deflection subjects the layers 14 and 16 of the sensor element 12 to a mechanical stress, so that charge carriers are shifted, due to the generally known piezoelectric effect, in the oppositely poled layers 14 and 16. This charge-carrier displacement leads to the generation of a voltage at the electrodes 20 and 22. The voltage being generated is proportional to the acceleration a, since a greater acceleration a results in a more vigorous deflection of the bending bar 46 and, thus, in a more pronounced piezoelectric effect. The voltage applied to the electrodes 20 and 22 is tapped off via the first contact regions 40 and 40' of the retaining means 26 and 28. Since the retaining means 26 and 28 consist of an electrically conductive material, the voltage signal produced by the sensor element 12 is applied simultaneously to their second contact regions 44 and 44'. The voltage signal from the sensor element 12 can be fed from the second contact regions 44 and 44' to an evaluation circuit (not shown in FIG. 1), which, in response to the magnitude of the voltage signal, detects a certain magnitude of the acceleration a and which may, for example, release a control signal to other devices, such as occupant-restraint systems in motor vehicles.

The design of the retaining means 26 and 28 enables the sensor element 12 to be fixed exactly in a position running normal to an assembly surface, so that the acceleration sensor 10 is able to detect a sensing direction running exactly parallel to the assembly surface. Thus, in detecting the acceleration a, one can essentially rule out those errors which are attributable to an imprecise alignment of the sensor element 12 to the assembly surface. Thus, regardless of how the acceleration sensor 10 is mounted on an assembly surface, it is ensured that the sensing direction of the sensor element 12 will always run parallel to the assembly surface. This facilitates the aligning of the sensor element 12, for example, to an acceleration acting essentially frontally on a motor vehicle for example, in order to trigger an airbag in a timely fashion.

FIG. 2 illustrates an acceleration sensor 10 according to another exemplary embodiment of the present invention. The parts that are equivalent to those in FIG. 1 are given the same reference numerals and are not elucidated again. In the case of the acceleration sensor 10 depicted in FIG. 2, the sensor element 12 is secured between the adjustment parts 38 and 38' of the holding module 24 so as to allow a bending bar 48 to be disposed on both sides of the adjustment parts 38 and 38'. Compared to the one-sided deflection of the sensor element 12 relative to the adjustment part 38 as shown in FIG. 1, in the exemplary embodiment depicted in FIG. 2, there is a two-sided deflection of the bending bar 48 relative to the adjustment part 38. The lengths selected for the bending bars 46 and 48 can be varied to allow for the different piezoelectric properties of the materials used for the layers 14 and 16 of the sensor element 12. The longer the free bending bar of the sensor element 12, the more possible is a deflection under the influence of an acceleration a. The degree of the deflection results in a certain mechanical straining of the sensor element 12, which, in turn, produces the piezoelectric effect. It is, thus, possible for the piezoelectric effect inherent in each material to be adjusted to a specific deflection of the sensor element 12.

Figure 3:
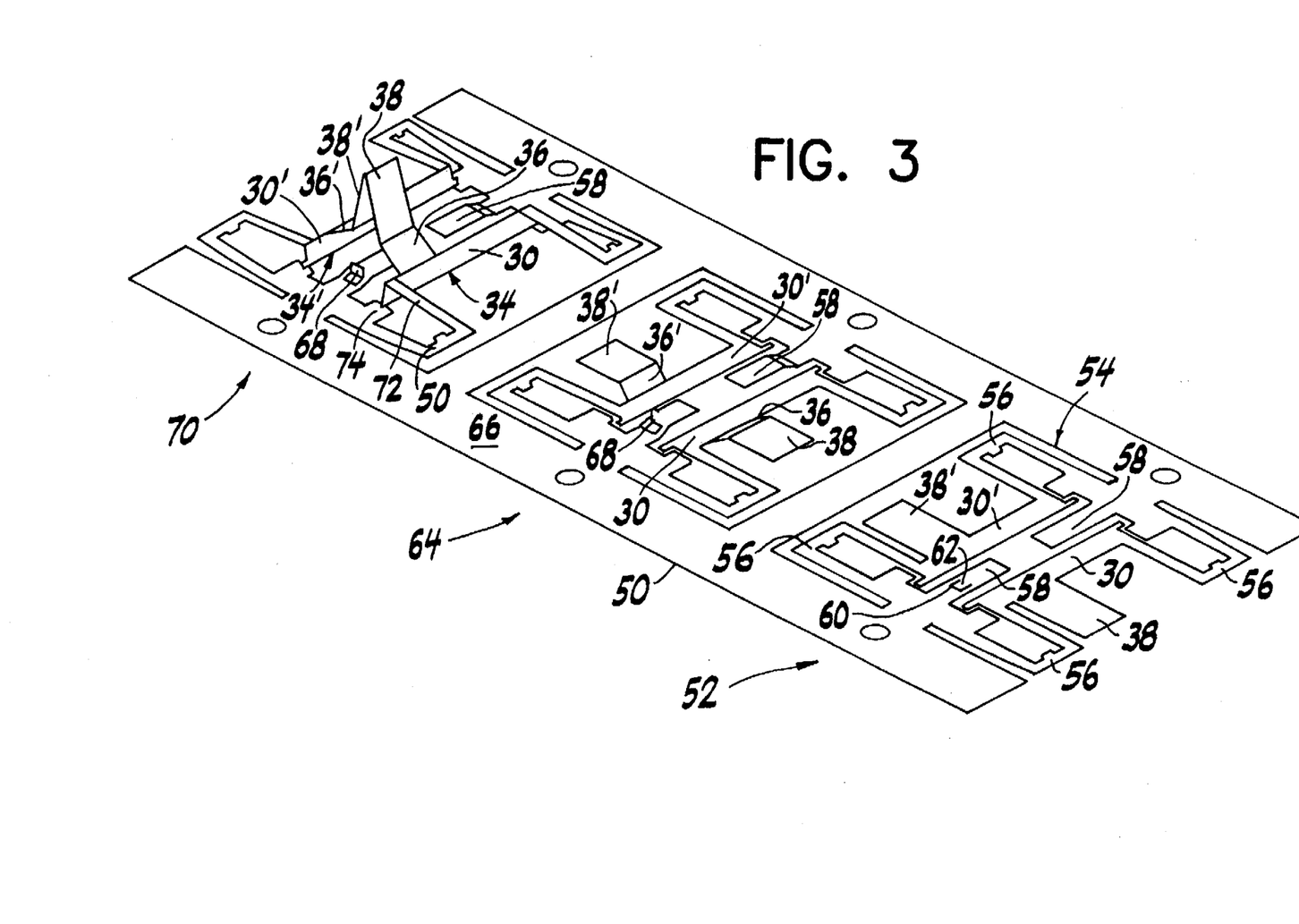
FIG. 3 depicts, schematically the steps for manufacturing a holding module according to the present invention
Figure 4:
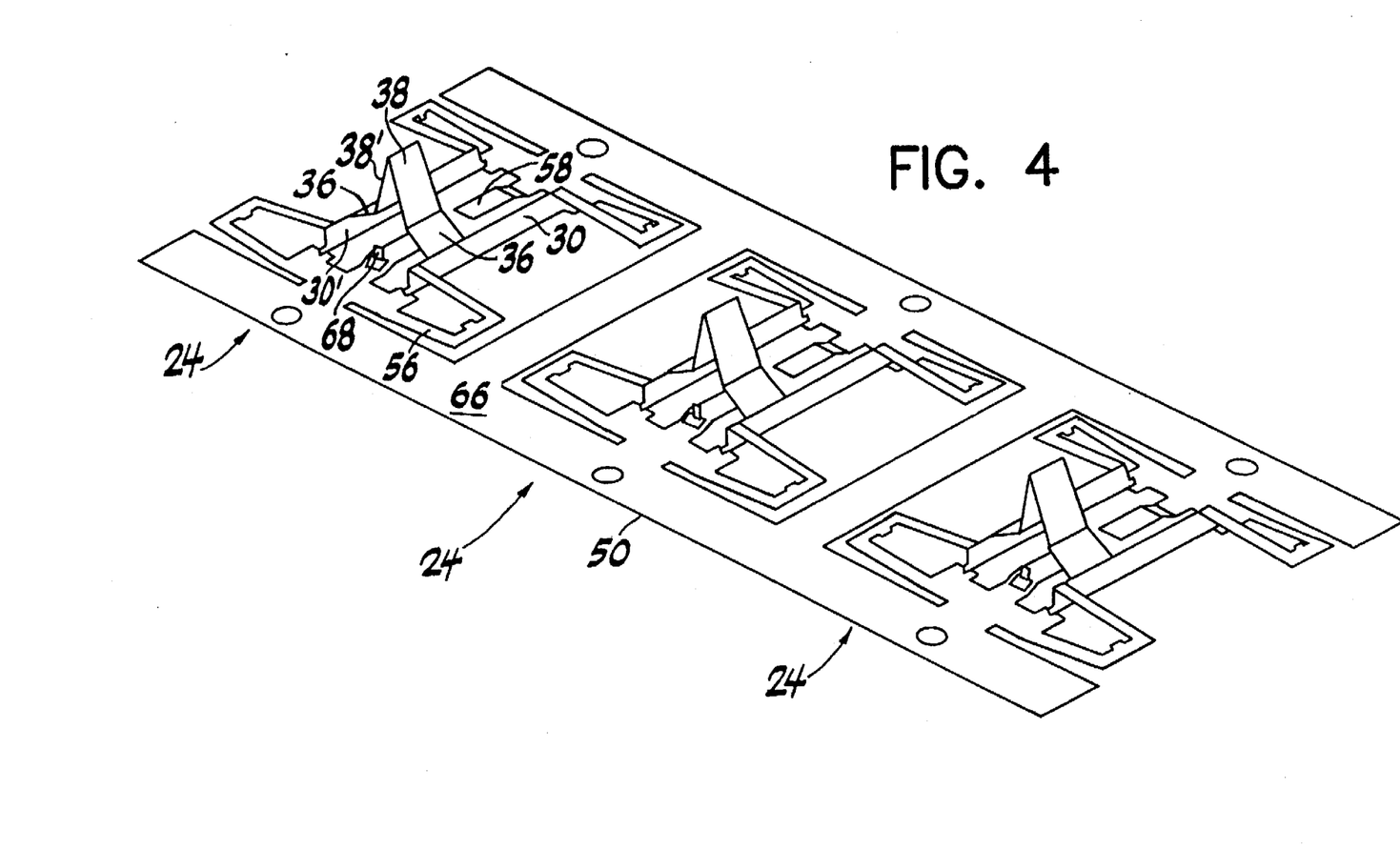
FIG. 4 depicts, schematically completed holding modules according to the present invention
Figure 5:
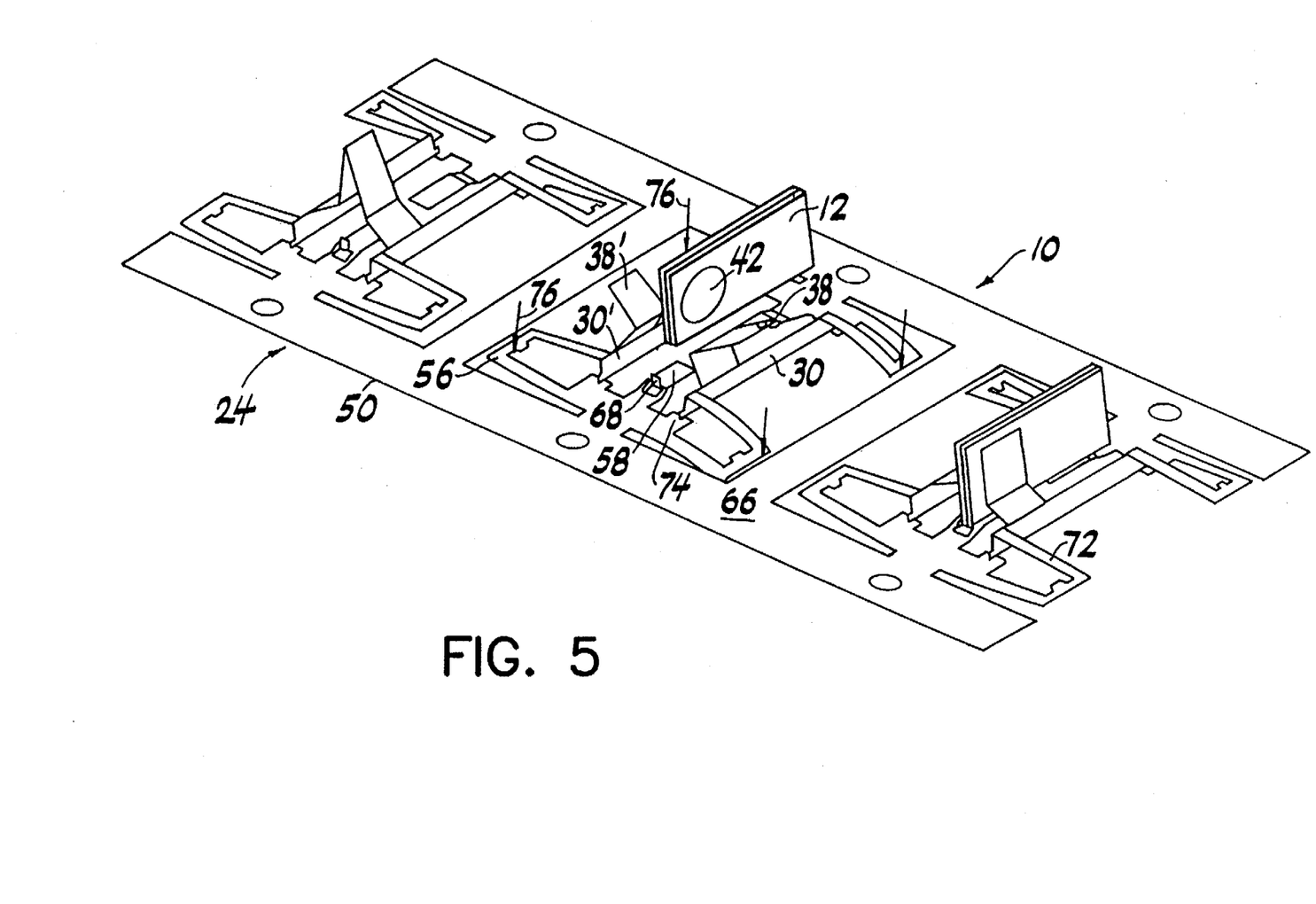
FIG. 5 depicts, schematically the assembly steps for manufacturing an acceleration sensor according to the present invention

FIGS. 3 through 5 elucidate the manufacturing of the acceleration sensor 10 shown in FIG. 1. FIG. 3 illustrates the process for manufacturing the holding module 24 of the acceleration sensor 10. In a first step 52, a contour 54 is punched out of a sheet steel strip 50 in conformance with the contour of the later holding module 24 and the contours of the substructures required for a later assembly of the sensor element 12. In particular, the base members 30 and 30' and the adjustment parts 38 and 38' are shown. The base members 30 are joined by way of torsion springs 56, which are sketched here, with the sheet metal strip 50. Tabs 58 originate at the sheet-metal strip 50 and run parallel to the base members 30 and 30'. One of the tabs 58 has a cut-out 60, so that a projection-type section 62 results.

In a second step 64, a bending-shaping process is carried out to produce the retaining webs 36 and 36' that join the adjustment parts 38 and 38' to the base member 30 and 30'. Furthermore, the tabs 58 are bent upwards, so that they are lifted above the level of the sheet metal strip 50, but come to rest parallel to a surface 66 of the sheet metal strip 50. The projection-type section 62 of the tab 58 with the cut-out 60 is bent upwards at the same time, at right angles to the tabs 58, i.e., to the surface 66, and forms a stop means 68.

In a third step 70, the base members 30 and 30' are first lifted slightly and then bent over at one arm 72 of the torsion springs 56, so that said base members come to rest with their end faces 34 and 34' on projections 74 arranged on the torsion springs 56. Folding over the base members 30 and 30' causes the retaining webs 36 and 36' with the contiguous adjustment parts 38 and 38' to be folded over at the same time, so that the adjustment part 38 lies elastically against the adjustment part 38'.

The manufacturing steps 52, 64 and 70 illustrated in FIG. 3 can be carried out continuously on an endless band of a sheet-metal strip 50 using suitable punching and bending tools, so that one attains the band shown in FIG. 4 with individual pre-fabricated holding modules 24. The holding modules 24 are still joined mechanically via the torsion springs 56 to the sheet-metal strip 50. Thus, depending on the length of the sheet-metal strip 50, one obtains a certain number of ready-made holding modules 24 situated in defined positions. A highly precise assembly operation can be achieved by properly selecting the punching tools and the bending devices, so that, in principle, a multiplicity of very simple and identically constructed holding modules 24 is attained.

The process for assembling the entire acceleration sensor 10 is elucidated in FIG. 5. A compressive force indicated by the arrows 76 is exerted on the torsion springs 56 causing the base members 30 and 30' to swivel around their supporting points on the projections 74, so that the adjustment parts 38 and 38' move apart. At this point, a sensor element 12 is introduced using a suitable device (middle representation) into the resulting clearance space between the adjustment parts 38 and 38'. The sensor element 12 comes to rest on the tabs 58 and abuts with an end face against the stop means 68. The adhesive agent 42, for example, can have previously been applied to the sensor element 12 in the regions opposing the adjustment part 38 and 38'. Such adhesive agent can be, for example, an electrically conductive adhesive agent that had been stamped on. After the sensor element 12 is positioned on the tabs 58, i.e., on the stop means 68, the compressive force 76 acting on the torsion springs 56 is removed, causing the base members 30 and 30' to swing back and the adjustment parts 38 and 38' to spring back toward the sensor element 12. The adhesive agent 42 provides a mechanical and electrically conductive coupling of the sensor element 12 to the adjustment parts 38 and 38' (first contact regions 40 and 40', FIG. 1), so that when properly cured, said adhesive agent 42 produces a durable, electrically conductive connection.

The exact position of the sensor element 12 in relation to the entire holding module 24 is determined by the adjustment parts 38 and 38', the tabs 58 and the stop means 68. It is, thus, possible to precisely align the sensor element 12 in the x-y-z direction. Thus, the geometric position of the sensor element 12 can be exactly defined in relation to a reference surface (top surface 66), which corresponds to a later mounting surface. In addition, the length of the bending bar 46 (FIG. 1) of the sensor element 12 can be determined by this means. The ready assembled acceleration sensors 10 can now be conveyed, for example, through a tunnel furnace, to allow the adhesive agent 42 to cure. In a last process step not shown in FIG. 5, the acceleration sensors 10 are cut apart. To this end, the arms 72 of the torsion springs 15 are cut through, e.g., by means of punching, laser cutting, or other suitable process steps. After the arms 72 are cut through, one attains the acceleration sensor 10 shown in FIG. 1.

Figure 6:
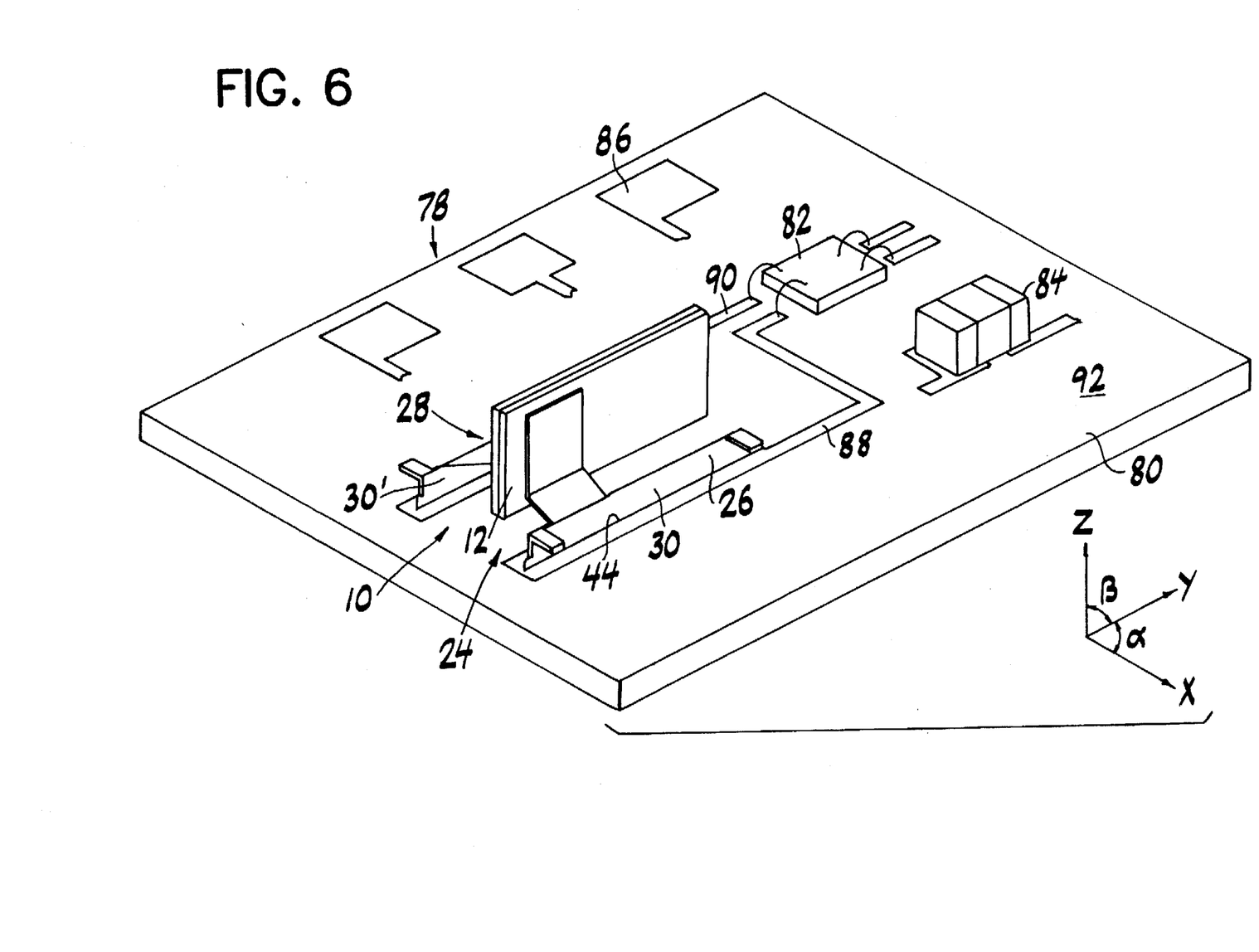
FIG. 6 depicts, schematically, a perspective view of a complete acceleration sensor unit according to the present invention
Figure 7:
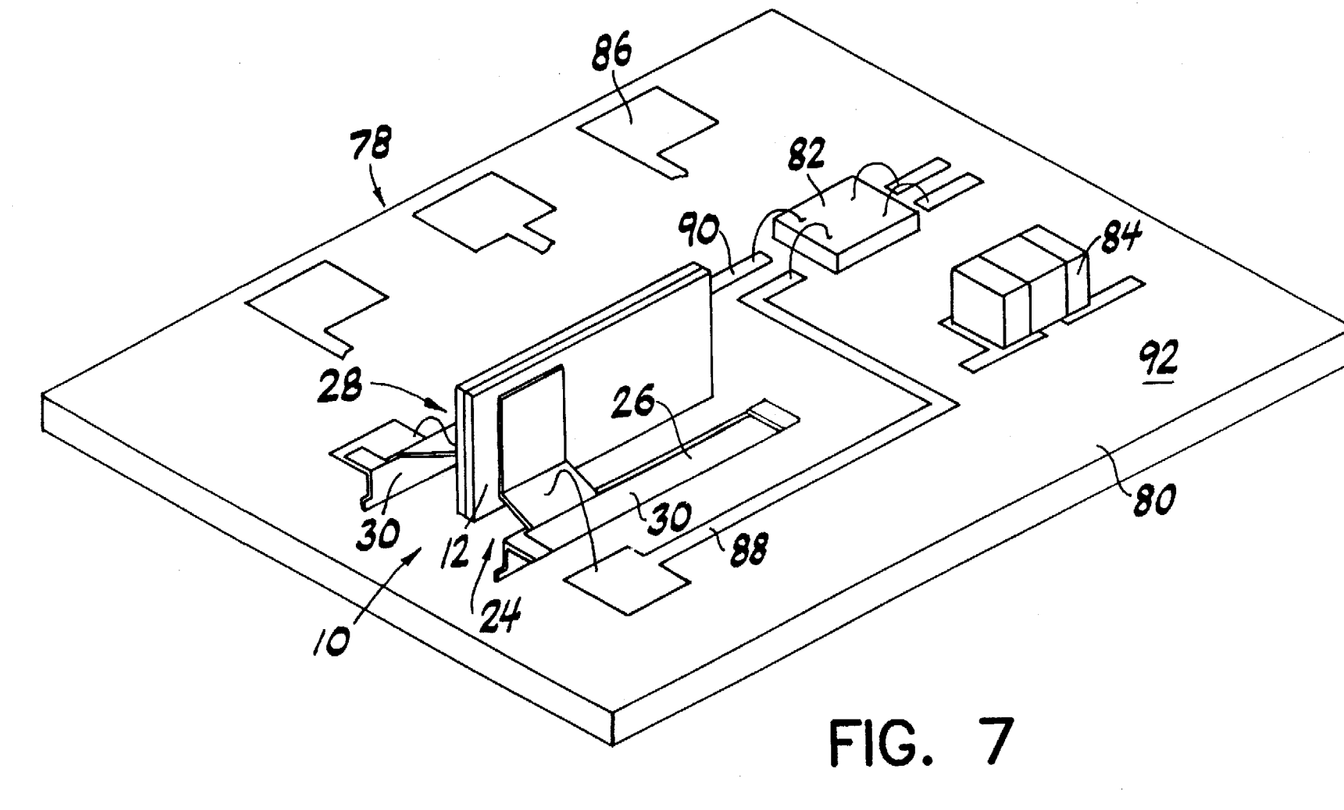
FIG. 7 depicts schematically, a perspective view of a complete acceleration sensor unit in accordance with a further exemplary embodiment of the present invention.

Complete acceleration sensor units 78 containing the acceleration sensor 10 are illustrated in FIGS. 6 and 7. The unit 78 has a supporting substrate 80, on which an evaluation circuit 82 is arranged. The evaluation circuit 82 can consist, e.g., of a chip containing integrated electronic circuits. The supporting substrate 80 can have, e.g., other electronic components 84 and connecting areas 86. Electrically conductive connections 88 and 90 lead from the evaluation circuit 82 to the acceleration sensor 10. The acceleration sensor 10 is so arranged with its retaining means 26 and 28 on the supporting substrate 80 that the bottom end faces 34 and 34' of the base members 30 and 30' forming the second contact regions 44 and 44' are respectively positioned directly on the connections 88 and 90 designed as printed-circuit traces. A fixed and electrically conductive connection can be established between the contact regions 44 and 44' and the connections 88 and 90, for example, by soldering on or by applying an electrically conductive adhesive agent. The voltage signals produced when the bending bar 46 of the sensor element 12 is deflected are thus transmitted over the shortest route directly via the retaining means 26 and 28 to the electrical connections 88 and 90 and, from said connections, to the evaluation circuit 82. Overall, therefore, very little outlay is required for assembly and wiring to mount the acceleration sensor 10 on the supporting substrate 80. The arrangement of the acceleration sensor 10 shown in FIG. 6 results in a sensing direction exactly parallel to a top surface 92 (mounting surface) of the supporting substrate 80. The sensing direction of the entire acceleration sensor unit 78 can be determined in dependence upon how the supporting substrate 80 is arranged on a component, e.g. of a motor vehicle. It is also possible, however, in accordance with an exemplary embodiment (not shown), to arrange the acceleration sensor 10 at a specific angle $\alpha$ on the top surface 92 and/or at a specific angle $\beta$ normal to the top surface 92. Thus, any desired sensing direction of the acceleration sensor unit 78 can be achieved by properly selecting the angles $\alpha$ and $\beta$. Therefore, by fitting the supporting substrate 80 with one single, simple-to-manufacture acceleration sensor 10, one attains acceleration-sensor units 78 suitable for different sensing directions.

FIG. 7 depicts another exemplary embodiment according to the present invention where the parts that are equivalent to those in FIG. 6 are given the same reference numerals and are not elucidated again.

The acceleration sensor 10 is placed with its holding module 24 directly on the top surface 92 of the supporting substrate 80. A mechanical connection can be established, e.g., by means of soldering, welding, or the like. The electrical contacting of the acceleration sensor 10 with the connections 88 and 90 leading to the evaluation circuits 82 is achieved by bonding on a wire between the connection 88 and the retaining means 26, or between the connection 90 and the retaining means 28. This makes it easily possible to arrange the acceleration sensor 10 at any desired angle $\alpha$ and/or $\beta$ (see FIG. 6) to the top surface 92 of the supporting substrate 80 and, at the same time, to establish an electrically conductive connection between the sensor element 12 and the evaluation circuit 82.

It is easily possible to manufacture an acceleration sensor 10, which has a simply constructed holding module 24, permitting both a mechanical as well as an electrically conductive coupling of the acceleration sensor 10 to a supporting substrate 80. The self-adjusting assembly process, enabled, in particular, by the formation of an x-y-z stop means on the adjustment parts 38 and 38', of the tabs 58 and of the stop means 68 for the sensor element 12, make it possible for the sensor element 12 to be definably aligned to the top surface 66 of the sheet-metal strip 50 that serves as a reference surface during the assembly operation. The tabs 58 and the stop means 68 serve merely as auxiliary mechanical stop means during the assembly operation and are discarded after the acceleration sensor 10 is separated off. It is, thus, possible to have a very precise arrangement of the sensor element 12, in particular by selecting the length of the bending bar 46 of the sensor element 12 in conformance with the entire holding module 24. Furthermore, by dispensing with the assembly aids for the sensor element 12, the sensor element 12 will be reliably prevented from coming to rest on the supporting substrate 80 during its normal operational use in an acceleration sensor unit 78. Thus, the sensor element 12 is able to deflect freely at any time in dependence upon the selected length of the bending bar 46 or of the bending bars 48. The holding module 24 is selectively designed to enable the sensor element 12 to be fixed securely in place already during the assembly operation, i.e., before or during the curing of the adhesive agent 42, so that additional auxiliary devices are not needed to hold the sensor element 12 in a specific position. Overall, therefore, there are no forces acting on the sensor element 12 during assembly, so that, for example, brittle materials, such as piezoelectric ceramics, may be employed here as well. Altogether, the simple and very precisely controllable punching and bending operations translate into a very precise assembly, so that inexpensive materials can be used for the holding module 24 and, all in all, only minimal costs are entailed in the manufacturing of the acceleration sensor 10. In particular, the acceleration sensor 10 can also be fabricated to be very small in size and extremely low in weight.

Within broad limits, one is able to freely select the stiffness desired of the holding module 24 for acceleration transfer by giving the holding module 24 an appropriate form design, e.g., bending edges, beads, etc. This makes it possible to achieve a favorable compromise among the mechanical transfer of shock accelerations (free fall), the natural resonant frequency of the sensor element 12 (flexural resonator), and the mechanical strain produced during the assembly operation on the supporting substrate 80. Due to the symmetrical design of the holding module 24, any possible transfer of heat into the sensor element 12 will likewise be symmetrical, so that the transfer of heat into the layers 14 and 16 of the sensor element 12 can be ideally compensated pyroelectrically because of their opposing polarization directions 18. The expansion coefficient of the material of the holding module 24 can, for example, be adapted to the material of the sensor element 12, thus, on the one hand, enabling a stress-free assembly, i.e., no excessive mechanical straining of the material of the sensor element 12 and, on the other hand, minimizing any ageing of the material of the sensor element 12 due to the stresses of temperature. Overall, therefore, the material for the holding module 24 can be selected from a material that is easy to process and is suitable, in particular, for cementing, soldering, or bonding. In some instances, the top surface of the holding module 24 can, for example, be treated over the entire surface or over part of the surface to improve cementing and soldering properties or bondability.

What is claimed is:

1. A method for manufacturing at least one sensor having one sensor element with piezoelectric layers contacted by at least one electrode, comprising the steps of:

providing at least one retaining member from a portion of sheet metal, the at least one retaining member having a base member and an adjustment part, and initially remaining joined with the portion of sheet metal;

joining the base member and the adjustment part using at least one retaining web;

coupling the adjustment part to the at least one electrode; and severing the at least one retaining member from the portion of sheet metal.

2. The method according to claim 1, further comprising the step of:

fashioning the retaining means by punching and bending-shaping operations.

3. The method according to claim 1, further comprising the steps of:

after severing the at least one retaining member from the portion of sheet metal, joining the base member to a supporting substrate; and coupling an evaluation circuit to the supporting substrate.

4. The method according to claim 1, further comprising the steps of:

fashioning the sensor element as a two-sided plate-shaped flexural element;

mounting a first electrode on a first side of the sensor element;

mounting a second electrode on a second side of the sensor element;

providing a first retaining member for the first electrode; and providing a second retaining member for the second electrode.

5. The method according to claim 4, wherein after the first and second retaining members are fashioned from the portion of sheet metal, a first adjustment part corresponding to the first retaining member and a second adjustment part corresponding to the second retaining member press against one another.

6. The method according to claim 5, wherein the first and second retaining member fashioned from the portion of sheet metal remain unitary with the portion of sheet metal through first and second torsion springs.

7. The method according to claim 6, further comprising the steps of:

applying a separating force to the first and second adjustment parts;

positioning the sensor element between the first and second adjustment parts;

removing the separating force from the first and second adjustment parts, so that the first and second adjustment parts press against the first and second electrodes of the sensor element; and coupling the first and second adjustment parts to the first and second electrodes respectively.

8. The method according to claim 7, wherein the first and second adjustment parts are coupled to the first and second electrodes, by soldering.

9. The method according to claim 7, wherein the first and second adjustment parts are coupled to the first and second electrodes by an electrically conductive adhesive.

10. The method according to claim 7, further comprising the steps of:

fashioning a stop member from the portion of sheet metal;

positioning the sensor element against the stop member, thereby determining a position of the sensor element relative to the first and second adjustment parts along a first, second and third axis.

11. An acceleration sensor, comprising:

a sensor element having piezoelectric layers, wherein at least one of the piezoelectric layers is coupled to an electrode;

at least one retaining member fashioned from a portion of sheet metal, the at least one remaining member having a base member and an adjustment part; and at least one retaining web joining the base member and the adjustment part, wherein the adjustment part is coupled to the at least one electrode.

12. The acceleration sensor according to claim 11, further comprising:

a supporting substrate, to which is coupled the base member; and an evaluation circuit coupled to the supporting substrate.

13. The acceleration sensor according to claim 11, wherein the sensor element includes a plate-shaped flexural sensor element having a first side and a second side; and further comprising:

a first electrode mounted on the first side of the sensor element;

a second electrode mounted on the second side of the sensor element;

a first retaining member for the first electrode;

a second retaining member for the second electrode;

a first adjustment part corresponding to the first retaining member; and a second adjustment part corresponding to the second retaining member, wherein the sensor element is positioned between the first and second adjustment parts and the first and second electrodes are coupled to the first and second adjustment parts, respectively.

14. The acceleration sensor according to claim 13, wherein the first and second adjustment parts are coupled to the first and second electrodes by soldering.

15. The acceleration sensor according to claim 13, wherein the first and second adjustment parts are coupled to the first and second electrodes by an electrically conductive adhesive.

16. The acceleration sensor according to claim 13, further comprising:

a stop member fashioned from the portion of sheet metal, for positioning the sensor element and thereby determining a position of the sensor element relative to the first and second adjustment parts along a first, second and third axis.

* * * * *